United States Patent [19]
Weiser

[11] Patent Number: 5,756,105
[45] Date of Patent: May 26, 1998

[54] OPACITY ASSOCIATED PROTEINS, DNA ENCODING THE SAME, AND METHODS OF USE THEREOF

[75] Inventor: Jeffrey N. Weiser, Merion, Pa.

[73] Assignee: Children's Hospital of Philadelphia, Philadelphia, Pa.

[21] Appl. No.: 332,576

[22] Filed: Oct. 31, 1994

[51] Int. Cl.⁶ .................. A61K 39/102; A61K 39/02; C12P 21/06; C07K 1/00
[52] U.S. Cl. .................. 424/256.1; 424/200.1; 435/69.1; 435/69.3; 530/350; 536/23.1; 536/23.7
[58] Field of Search .................. 424/200.1, 256.1; 530/350; 536/23.7, 23.1; 435/69.1, 69.3

[56] References Cited

U.S. PATENT DOCUMENTS 5,108,744  4/1992  Deich et al. .................. 424/92

OTHER PUBLICATIONS

Barenkamp, "Outer Membrane Proteins and Lipoplysaccharides of Nontypeable *Haemophilus influenzae*" *J. Infect. Disease* 165 (Supp.1): s181–s184 (1992).

Weiser et al., "Characterization of Repetitive Sequences Controlling Phase Variation of *Haemophilus influenzae* Lipopolysaccharide" *J. Bact.* 172(6): 3304–3309 (1990).

Anderson et al., "Human Serum Activities Against *Hemophilus Influenzae*, Tybe B" *J. Clin. Invest.* 51: 31–38 (1972).

Anderson and Smith, "Immunogenicity in Weanling Rabbits of a Polyribophosphate Complex from *Haemophilus Influenzae* Type B" *J. Inf. Dis.* 136 (Suppl) S63–S70 (1977).

Barenkamp, "Protection by Serum Antibodies in Experimental Nontypable *Haemophilus Influenzae* Otitis Media" *Infect. Immun.* 52: 572–578 (1986).

Braun "Bacterial Genetics" Philadelphia: WB Saunders 153–183 (1965).

Gilsdorf and Ferrieri, "Susceptibility of Phenotypic Variants of *Haemophilus Influenzae* Type B to Serum Bactericidal Activity: Relation to Surface Lipopolysaccharide" *J. Infect. Disease* 153: 223–231 (1986).

Kupsch et al., "Variable Opacity (Opa) Outer Membrane Proteins Account for the Cell Tropisms Displayed by *Neisseria Gonorrhoeae* for Human Leukocytes and Epithelial Cells" *EMBO J.* 12: 641–650 (1993).

Makela et al., "Polysaccharide Vaccines of Group A *Neisseria Meningitidis* and *Haemophilius Influenzae* Type B: A Field Trial in Finland" *J. Inf. Dis.* 136 (Suppl) S43–S50 (1977).

Musher et al., "Opsonizing and Bactericidal Effects of Normal Human Serum on Nontypable *Haemophilus Influenzae*" *Infect. Immun* 39: 297–304 (1983).

Parke, Jr. et al., "Interim Report of a Controlled Field Trial of Immunization with Capsular Polysaccharides of *Haemophilus Influenzae* Type B and Group C *Neisseria Meningitidis* in Mecklenburg County, North Carolina (Mar. 1974–Mar. 1976)" *J. Inf. Dis.* 136 (Suppl): S51–S56 (1977).

Pittman, "Variation and Type Specificity in the Bacterial Species *Hemophilus Influenzae*" *J. Exp Med* 53: 471–492 (1931).

Weiser et al., "Phase–Variable Lipopolysaccharide Structures Enhance the Invasive Capacity of *Haemophilus Influenzae*" *Infect. Immun.*, 58: 3455–3457 (1990).

Weiser et al., "Identification of a Chromosomal Locus for Expression of Lipopolysaccharide Epitopes in *Haemophilus Influenzae*" *Infect. Immun.* 57: 3045–3052 (1989).

Weiser, "Relationship Between Colony Morphology and the Life Cycle of *Haemophilus Influenzae*: The Contribution of Lipopolysaccharide Phase Variation to Pathogenesis", Journal of Infectious Diseases 168: 672–680 (1993).

Zwahlen et al., "Alteration of the Cell Wall of *Haemophilus Influenzae* Type B by Transformation with Cloned DNA: Association with Attenuated Virulence" *J. Infect. Dis.* 152: 485–492 (1985).

Zwahlen et al., "Contribution of Lipopolysaccharide to Pathogenicity of *Haemophilus Influenzae*: Comparative Virulence of Genetically–Related Strains in Rats" *Microb. Pathog.*, 1: 465–73 (1986).

*Primary Examiner*—James C. Housel
*Assistant Examiner*—Jennifer Shaver
*Attorney, Agent, or Firm*—Woodcock Washburn Kurtz Mackiewicz & Norris LLP

[57] ABSTRACT

Opacity associated proteins and DNA encoding the same are provided by the present invention. Opacity associated proteins are membrane proteins of *H. influenzae* which are useful as immunogens in vaccines against infection by *H. influenzae*. Recombinant cells transformed with DNA encoding opacity associated proteins and vectors encoding the same are also provided and are useful in and for the preparation of vaccines against *H. influenzae* infection. Antibodies against opacity associated proteins are also described. Methods of detecting *H. influenzae* in a sample and methods of immunizing mammals against *H. influenzae* are also provided.

4 Claims, 12 Drawing Sheets

FIG.1A

```
AAATCTATAA AACCTTGCAA TCTCTGACTT CTGGCTATCT TGTTCCTAAA CTTGCACGAG      60

AAATTGCGGG CGAGCCAAAT AAGACTTTAT ACGCAGAATA AGATCCGATA AAATACACAT     120

AATTTTTTCG CCGCACTTTT GAGCTTCTCA ATTTTGTGGC TAATTAATAT AAATAAGAAC     180

AAGCATCAGA GGCAATCCAG TGAATTCT ATG GAT AAA AAT CAA CAA TCA TCT       232
                                Met Asp Lys Asn Gln Gln Ser Ser
                                 1               5

CAA AAT GAA TTG GAT TTA GGG CTT AAT CAA GAG CCA ATT ACA CCA AAG      280
Gln Asn Glu Leu Asp Leu Gly Leu Asn Gln Glu Pro Ile Thr Pro Lys
         10                  15                  20

AAA ACA ATT CAG CCA AGT TCG TCA ATT TTA GGT AAA GCA AAA GGG TTA      328
Lys Thr Ile Gln Pro Ser Ser Ile Leu Gly Lys Ala Lys Gly Leu
 25                  30                  35                  40

TTT GCC AAA AAA AAT CAC GTG CAA ACT AAC TTT CAG CAA CGT AAA GAA      376
Phe Ala Lys Lys Asn His Val Gln Thr Asn Phe Gln Gln Arg Lys Glu
                 45                  50                  55
```

FIG.1B

```
CCT ACT TTT GGC GAT TCA TCA ACG CAA GAA AAT GAT CCT TTA ATT CCG    424
Pro Thr Phe Gly Asp Ser Ser Thr Gln Glu Asn Asp Pro Leu Ile Pro
             60                      65                      70

AGT GAA AAT TTG AAA AAA GTG CAA AAG CCT GTT CTT CAA ACT TCT TCC    472
Ser Glu Asn Leu Lys Lys Val Gln Lys Pro Val Leu Gln Thr Ser Ser
             75                      80                      85

ACA GAA GAA AAT ATT TCT GCG GTT GAT GAA GAA ATC AGT GCT GAA AAT    520
Thr Glu Glu Asn Ile Ser Ala Val Asp Glu Glu Ile Ser Ala Glu Asn
             90                      95                     100

AAC GCG GAT GAA CCC GTC GAA AAG GCT GAA AAA CCT ATT TTA GCT CAA    568
Asn Ala Asp Glu Pro Val Glu Lys Ala Glu Lys Pro Ile Leu Ala Gln
105                     110                     115                 120

CCA GAA AAA TGG AAA ATA TTA CAA GTA TTG CCA GCA AAA CAT CGC CGT    616
Pro Glu Lys Trp Lys Ile Leu Gln Val Leu Pro Ala Lys His Arg Arg
            125                     130                     135
```

FIG.1C

```
TTA TTT ATG GCT ATT TTT GTG TTG GTT ATT TTA TTG ATT TTC TTC    664
Leu Phe Met Ala Ile Phe Val Leu Val Ile Leu Leu Ile Phe Phe
        140                 145                 150

GCA TTA AAA CCA AGT TCT GAC ACC GTT GAG TCT TTT ACT CAA TCT AAC    712
Ala Leu Lys Pro Ser Ser Asp Thr Val Glu Ser Phe Thr Gln Ser Asn
        155                 160                 165

AGC AAT GAA GTT CCT GTG CAG TTC CAA TCG TTA GAT CAA AGT CAG CCA    760
Ser Asn Glu Val Pro Val Gln Phe Gln Ser Leu Asp Gln Ser Gln Pro
        170                 175                 180

CTG GAA ACC ACG ATT TTA GAT AAT CCT GCA CAA CAA AAT CAA ATG GCT    808
Leu Glu Thr Thr Ile Leu Asp Asn Pro Ala Gln Gln Asn Gln Met Ala
        185                 190                 195                 200

GTA GAA CAA AAC CAA TCT GAA TTT GCA CCA AAA GCA GAG GAA GCG    856
Val Glu Gln Asn Gln Ser Glu Phe Ala Pro Lys Ala Glu Glu Ala
        205                 210                 215

GCG AAT AAT ACG ACG GCT CAA AAC CCA TTA GTA GAA AAT GCG CCA ATG    904
Ala Asn Asn Thr Thr Ala Gln Asn Pro Leu Val Glu Asn Ala Pro Met
        220                 225                 230
```

FIG.1D

```
CAA CAA AAT GTT GTT CAA TCT CCA AGT CAA ATG CCA AAT GAA ATG GCT      952
Gln Gln Asn Val Val Gln Ser Pro Ser Gln Met Pro Asn Glu Met Ala
        235                 240                 245

GCG GCA TCT GTT GCG CCT ATG CAA CCA GCT CAA GCG GAA CAG CCA AAA     1000
Ala Ala Ser Val Ala Pro Met Gln Pro Ala Gln Ala Glu Gln Pro Lys
    250                 255                 260

GCA ACT GTG CCA GTT CAG CCG ATG AAA AAA GCG GTA GAG CCA CAA CTT     1048
Ala Thr Val Pro Val Gln Pro Met Lys Lys Ala Val Glu Pro Gln Leu
265                 270                 275                 280

GCG CAT AAA GAT ACA GTG AAA AAA GAA GTG AAA GTG GCG GAG AAA GCA     1096
Ala His Lys Asp Thr Val Lys Lys Glu Val Lys Val Ala Glu Lys Ala
                285                 290                 295

CAG GCT CCA GCA AAA GCA ACG GAA CAA AAC GTC GCT AAA ACA GCA GGA     1144
Gln Ala Pro Ala Lys Ala Thr Glu Gln Asn Val Ala Lys Thr Ala Gly
            300                 305                 310
```

FIG.1E

```
AAC GCA CCG ATT GTT GAA GCC AAA CCT GTT CAA GCT AAA AAA GAA AAG    1192
Asn Ala Pro Ile Val Glu Ala Lys Pro Val Gln Ala Lys Lys Glu Lys
        315                 320                 325

AAA GTT CAA ATC GTT GAT GCA AAA CCT GTG AGT AAA CCT GTG AGT TCT ACA GCT TCT    1240
Lys Val Gln Ile Val Asp Ala Lys Pro Val Ser Lys Ser Thr Ala Ser
        330                 335                 340

CGC CTT TCA GCA AAA ACA TTA ACT GTG CCG AAA GGT GTT TCG CTG ATG    1288
Arg Leu Ser Ala Lys Thr Leu Thr Val Pro Lys Gly Val Ser Leu Met
        345                 350                 355                 360

CAA CTC TTC CGT GAT AAT CAA CTT AAT ATT TCC GAT GTA AAC GCA ATG    1336
Gln Leu Phe Arg Asp Asn Gln Leu Asn Ile Ser Asp Val Asn Ala Met
        365                 370                 375

AGC AAA GCG ACA GGG GCG GGA AAT GTT TTA AGT AGC TTT AAA TCT GGC    1384
Ser Lys Ala Thr Gly Ala Gly Asn Val Leu Ser Ser Phe Lys Ser Gly
        380                 385                 390

GAT AAA GTA ACG GTA TCT GTG AAT AAT CAA GGG CGA GTA AAT GAA ATG    1432
Asp Lys Val Thr Val Ser Val Asn Asn Gln Gly Arg Val Asn Glu Met
        395                 400                 405
```

FIG.1F

```
CGT TTA TCC AAT GGT GCG CGT TTT GTG CGT CAG TCT GAT GGT TCT TAT       1480
Arg Leu Ser Asn Gly Ala Arg Phe Val Arg Gln Ser Asp Gly Ser Tyr
    410                 415                 420

CAA TAT AAA AAA TAATTTTTTG GGGAGTAAT CGCCTTTTTC TTTTAAGTT             1532
Gln Tyr Lys Lys
425

CTTTCTCAA GGTAGGATTT ATG TTG AAA AAA ACA TCT CTT ATT TTT ACC          1582
                    Met Leu Lys Lys Thr Ser Leu Ile Phe Thr
                     1                   5                  10

GCA CTT TTA ATG ACT GGC TGT GTG CAA AAT GCG AAT GTA ACA ACA CCT       1630
Ala Leu Leu Met Thr Gly Cys Val Gln Asn Ala Asn Val Thr Thr Pro
            15                  20                  25

CAA GCG CAA AAA ATG CAA GTA GAA AAA ATG GAT AAA GCC TTA CAA AAA       1678
Gln Ala Gln Lys Met Gln Val Glu Lys Met Asp Lys Ala Leu Gln Lys
        30                  35                  40

GGC GAA GCT GAT CGA TAT TTA TGT CAA GAT GAT AGA GTT GTT CGT GTT       1726
Gly Glu Ala Asp Arg Tyr Leu Cys Gln Asp Asp Arg Val Val Arg Val
    45                  50                  55
```

FIG.1G

```
GTA CAC GCC ACG CAT AAA AAA TAC AAA AAA AAT TTG CAT TAT GTT ACT       1774
Val His Ala Thr His Lys Lys Tyr Lys Lys Asn Leu His Tyr Val Thr
 60                      65                      70

GTC ACT TTT CAA GGC GTA TCA GAA AAA CTA ACC TTA ATG ATT TCT GAA       1822
Val Thr Phe Gln Gly Val Ser Glu Lys Leu Thr Leu Met Ile Ser Glu
 75                      80                      85                90

CGT GGT AAA AAT TAC GCC AAT ATT CGT TGG ATG TGG CAA GAG CGT GAT       1870
Arg Gly Lys Asn Tyr Ala Asn Ile Arg Trp Met Trp Gln Glu Arg Asp
             95                     100                     105

GAT TTT AGT ACG CTA AAA ACG AAT CTC GGC GAA ATT TTA GCA ACG CAA       1918
Asp Phe Ser Thr Leu Lys Thr Asn Leu Gly Glu Ile Leu Ala Thr Gln
         110                     115                     120

TGT GTC TCA CAA ACA AGT GAA CGC TTA TCT GAC AAT AAT CGT GCA AAG       1966
Cys Val Ser Gln Thr Ser Glu Arg Leu Ser Asp Asn Asn Arg Ala Lys
     125                     130                     135

CGA ACT TCA ACG TGG TTT TGT TTT GCA TCG CCC TTA TAGTGAAACG            2015
Arg Thr Ser Thr Trp Phe Cys Phe Ala Ser Ser Pro Leu
 140                     145                     150

AGCTTATTGG TAGATTTATT CACTGAAGAA AGTGGGCGTT TAACCGTGAT TGCAAAAGGG     2075

GCGCGGGCAA AGCGTTCATC TTGGA                                           2100
```

OPACITY ASSOCIATED PROTEINS, DNA ENCODING THE SAME, AND METHODS OF USE THEREOF

FIELD OF THE INVENTION

This invention relates to compositions and methods for the preparation of opacity associated proteins and peptides such as Oap A and Oap B of *Haemophilus influenzae*. The proteins and peptides are used as immunogens in vaccine formulations for active immunization and for generation of antibodies for use in passive immunization.

The proteins and peptides can be obtained by purification from *H. influenzae* or produced using either recombinant DNA or chemical synthetic methods. Additionally the invention relates to novel DNA sequences and vectors useful for directing expression of Oap A and Oap B proteins and peptides. Diagnostic assays and kits are also provided.

BACKGROUND OF THE INVENTION

*Haemophilus influenzae* is a common resident on human mucosal surfaces, particularly the nasopharynx. Although it is usually in a commensal relationship with its host, it is also frequently identified in upper and lower respiratory tract infections of adults and children, in whom it remains a leading cause of bacterial disease such as bacterial meningitis, otitis media, epiglottitis and pneumonia. Moxon and Wilson, *Rev Infect Dis* 13 (suppl): 53183–53187 (1991).

*H. influenzae* infections have been traditionally treated with antibiotics. However, antibiotic resistant strains of pathogens have recently been reported, compromising antibiotic therapy *Center for Disease Control*, Morbidity and Mortality Weekly Rep., 23: 77, 1974. As a consequence, the common use of antibiotics to treat *H. influenzae* infections is questioned, and may be responsible in part for increasing frequency of resistance. Accordingly, new methods for the prevention and treatment of infection by *H. influenzae* are greatly desired.

The use of bacterial and viral vaccines has been very successful in the prevention of infectious diseases in humans and other mammals. Antigenic components have been isolated and purified from *H. influenzae* type b and have been used as vaccines. For example, purified capsular polysaccharide material of *Haemophilus influenzae* type b has been used as a vaccine against the meningitis caused by this organism in humans (Parke et al., J. Inf. Dis. 136 (Suppl.): S51, 1977; Anderson et al., *J. Inf. Dis.*, 136 (Suppl): S63, 1977; Makela et al., *J. Inf. Dis.* 136 (Suppl): S43, 1977). However, until now there was not a vaccine which is effective against all types of *Haemophilus influenzae* infection. Accordingly, the need for an effective, safe vaccine against all *Haemophilus influenzae* strains is greatly desired.

OBJECTS OF THE INVENTION

It an object of the invention to provide a vaccine formulation that elicits a protective immune response against typable and non-typable *H. influenzae*.

It is another object of the invention to provide probes useful in diagnostic tests for the presence of *H. influenzae* infection.

SUMMARY OF THE INVENTION

In accordance with the present invention are provided novel opacity proteins which are crucial to the ability of *H. influenzae* to colonize in the nasopharynyx of a host. Vaccine formulations encompassing at least one of the opacity proteins are provided by the present invention. In accordance with other aspects of the present invention, DNA sequences encoding opacity proteins of the present invention are provided. Said DNA sequences, encompassed in recombinant vectors, transformed into recombinant host cells and used in vaccine formuations, are also provided in accordance with the present invention. Monoclonal antibodies against opacity associated proteins of the present invention are also provided.

In accordance with other aspects of the present invention diagnostic assays are provided for the detection of *H. influenzae*. In addition, kits comprising diagnostic probes or peptides for diagnostic assays are provided.

BRIEF DESCRIPTION OF THE FIGURES

FIGS. 1A–1G are the DNA and putative amino acid sequence of Oap A and Oap B.

DETAILED DESCRIPTION

Figure 2A:
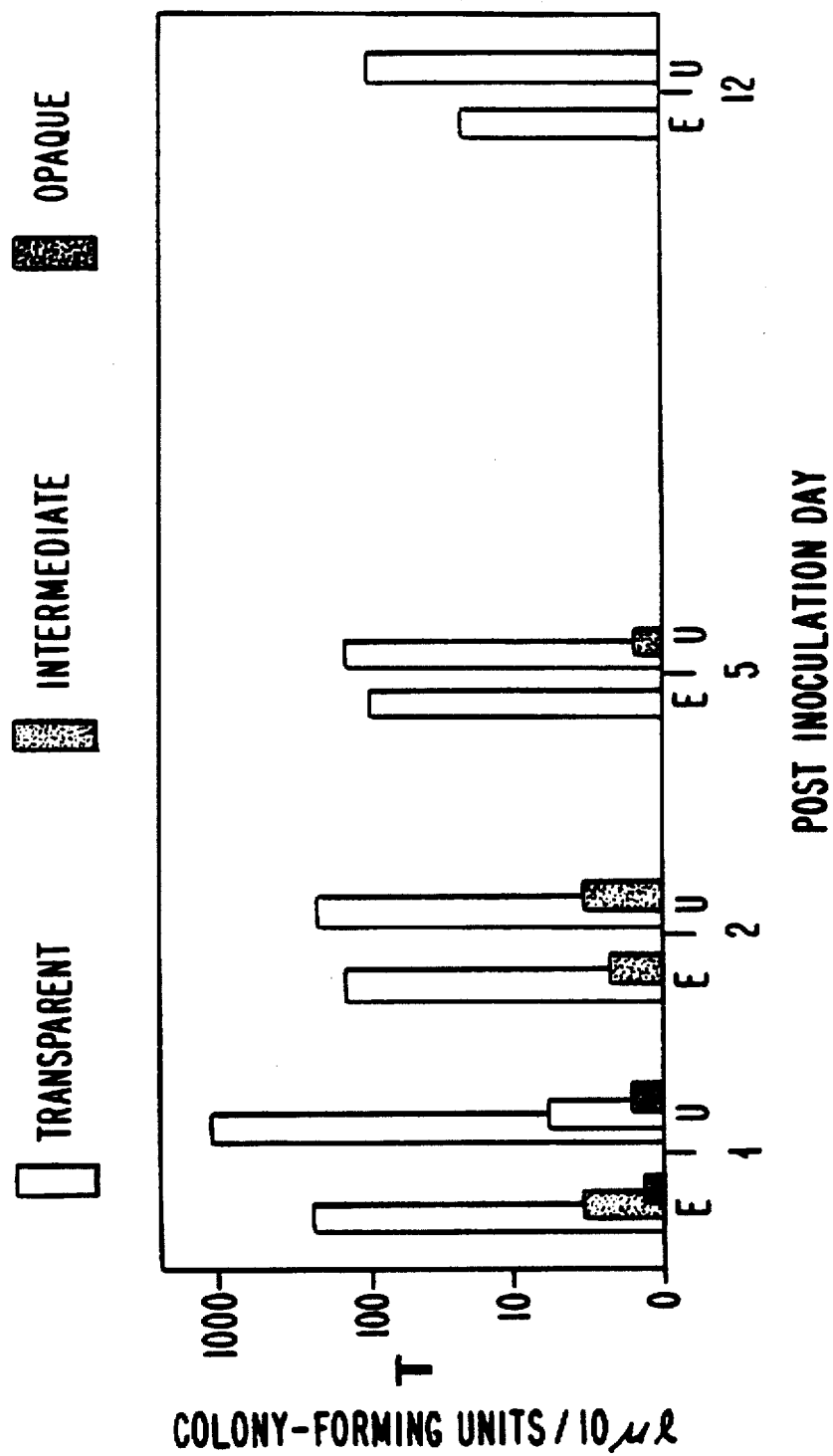
FIGS. 2A–2C are bar graphs showing the relationship between colony morphology and nasopharyngeal colonization. Arithmetic mean number of organisms of each phenotype in nasopharyngeal cultures on indicated days after inoculation are shown.

The present invention generally relates to vaccines and their use for preventing, ameliorating or treating *Haemophilus influenzae* infections.

Phenotypic variation appears to be an important mechanism by which bacterial pathogens adapt to varied environmental challenges encountered in distinct ecologic niches during colonization and infection. In some cases phenotypic variation is readily apparent as differences in colony morphology. Braun, "Bacterial Genetics" Philadelphia: WB Saunders 153–183 (1965). In fact, variations in colonial morphology have provided important clues toward understanding the host-parasite interaction in *H. influenzae* and other mucosal pathogens. Braun, "Bacterial Genetics" Philadelphia: WB Saunders 153–183 (1965), Pittman, *J. Exp Med* 53: 471–492 (1931). For example, alterations in colony morphology of *Neisseria gonorrhoeae* and *Neisseria meningitidis* have been shown to correlate with the expression of a family of outer membrane proteins referred to as opacity proteins, which have been implicated in bacterial attachment to specific host cell types. Kupsch et al., *EMBO J.* 12: 641–650 (1993). Applicants have identified two variable opacity (Oap) membrane associated proteins which are expressed by *H. influenzae* and appear to be implicated in the ability of *H. influenzae* to colonize and thereby to cause infection. The DNA and putative amino acid sequences of OapA and OapB are set forth in FIG. 1.

An immune response to one or both of these membrane associated proteins can be elicited in order to prevent or limit colonization of *H. influenzae* in the nasopharynx. Such an immune response can be invoked by administration of substantially pure Oap A and Oap B protein as the antigenic component. Substantially pure, in accordance with some embodiments of the present invention is greater than about 50% purity. Greater than about 85% purity is preferred in some embodiments of the present invention and greater than about 90% is still more preferred. In some embodiments of the present invention greater than about 95% purity is preferred.

The present invention is directed to opacity associated (Oap) proteins and peptides of *H. influenzae*. Specifically, the present invention is directed to Oap A and Oap B. The proteins and peptides of the invention can be produced using recombinant DNA method or by chemical synthesis. The Oap A and Oap B proteins and peptides can be used as immunogens in various vaccine formulations to protect against infection by *H. influenzae*, both typable and non-typable.

The present invention further relates to the nucleotide sequences of DNA encoding Oap A and Oap B proteins as well as the amino acid sequences of the Oap A and Oap B proteins and polypeptide fragments thereof.

According to one embodiment of the present invention, recombinant DNA techniques are used to insert nucleotide sequences encoding Oap A and/or Oap B into expression vectors that direct expression of the sequences in appropriate host cells. These expression vector-host cell systems can be used to produce *H. influenzae* opacity associated proteins, Oap A and Oap B and related proteins and peptides.

The gene products can be purified from cells in culture and used as immunogens in vaccine formulations. Alternatively, the proteins can be chemically synthesized. Preferably proteins have sequences substantially homologous to the sequence set forth in SEQ ID NO: 2 and SEQ ID NO: 3. In preferred embodiments of the present invention proteins are at least 85% homologous. In still other preferred embodiments said proteins are at least 95% homologous. In yet other preferred embodiments said proteins are 100% homologous. Such proteins are used in synthetic vaccine formulations.

Where the expression vector is a recombinant virus, the virus itself may be used as a vaccine. Infectious recombinant viruses that express one or both Oap A and Oap B proteins, and that do not cause disease in the host, can be used in live virus vaccine preparations to provide substantial immunity. Alternatively, inactivated virus vaccines can be prepared using "killed" recombinant viruses that express one or both Oap A and Oap B proteins.

The present invention is further directed to polyvalent antiserum and monoclonal antibody against one or both Oap proteins, as well as methods for use of such immunoglobulins for passive immunization. Diagnostic assays for *H. influenzae* are also provided.

The Oap gene, SEQ ID NO: 1 or a DNA sequence substantially homologous to SEQ ID NO: 1 can be prepared synthetically, or isolated from natural sources by methods known to those skilled in the art. Portions of the DNA sequence may also be prepared for use in some embodiments of the present invention. For example, probes may be prepared for diagnostic purposes. In preferred embodiments of the present invention the DNA sequence is 85% homologous to SEQ ID NO:1. In still other preferred embodiments of the present invention the DNA sequence is 95% homologous to SEQ ID NO: 1. In yet other embodiments of the present invention the DNA sequence is 100% homologous to SEQ ID NO: 1.

For some purposes it may be useful to substitute nucleotide analogs for naturally occuring nucleotides. For example, for use as nucleotide probes, nucleotide analogs such as nucleotides having 2' modification or backbone modifications may be preferred. Preparation of oligonucleotides comprising nucleotide analogs is known to those skilled in the art.

For insertion of the Oap gene into an expression vector, a vector is selected having the necessary elements for transcription and translation of the inserted protein coding sequence. A variety of host-vector systems may be employed to express opacity associated proteins, as long as the vector is compatible with the host cell system selected.

Expression systems useful in the present invention include, but are not limited to bacteria transformed with bacteriophage DNA, plasmid DNA or cosmid DNA, microorganisms such as yeast containing yeast vectors (e.g. *Saccharomyces cerevisiae*), mammalian cell systems such as VERO, Hela and CHO cells infected with a vectors having viral control elements (e.g. vaccinia, adenovirus, simian virus 40 etc.) and insect cell systems (e.g. baculovirus).

Depending upon the expression system selected, any of a variety of suitable transcription and translation elements may be used. Promoter sequences which enhance levels of transcription are preferably selected. The promoter used will, however, depend upon the system selected. Commonly used procaryotic control sequences include promoters for transcription initiation, optionally with an operator, along with ribosome binding site sequences, include such commonly used promoters as the beta-lactamase (penicillinase) and lactose (lac) promoter systems (Chang, et al., *Nature* (1977) 198:1056) the tryptophan (trp) promoter system (Goeddel, et al. *Nucleic Acids Res* (1980) 8:4057) and the lambda derived $P_L$ promoter and N-gene ribosome binding site (Shimatake, et al., *Nature* (1981) 292:128). Control sequences for yeast vectors include promoters for the synthesis of glycolytic enzymes. Additional promoters known in the art include the promoter for 3-phosphoglycerate kinase (Hitzeman, et al., *J Biol Chem* (1980) 255:2073), and those for other glycolytic enzymes such as glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase. Other promoters, which have the additional advantage of transcription controlled by growth conditions are the promoter regions for alcohol dehydrogenase 2, isocytochrome C, acidphosphatase, degradative enzymes associated with nitrogen metabolism, and enzymes responsible for maltose and galactose utilization (Holland, ibid). Expression vectors for mammalian cell systems ordinarily include promoters and control sequences compatible with mammalian cells such as, for example, the commonly used early and late promoters from Simian Virus 40 (SV 40) Fiers, et al., *Nature* (1978) 273:113), or other viral promoters such as those derived from polyoma, Adenovirus 2, bovine papilloma virus, or avian sarcoma viruses.

Bacterial host cell strains and expression vectors may be chosen which inhibit the action of the promoter unless specifically induced. In certain operons, the addition of specific inducers in necessary for efficient transcription of the inserted DNA. For example, the lac operon is induced by the addition of lactose or isopropylthio-beta-D-galatoside (IPTG). A variety of other operons, such as trp, pro, etc. are under different controls. Thus, expression of Oap proteins by an expression system can be controlled. This is especially of value in cases where the protein product is lethal or detrimental to the host cells. In such cases, cells may be cultured in conditions where the promoter is not induced in order to reach optimal cell density. Upon reaching optimal density, the promoter may be induced to express the gene of interest.

When cloning in eucaryotic cells, enhancer sequences are useful to optimize expression. For example, a 72 bp tandem repeat of SV40 DNA or the retroviral long terminal repeats (or LTRs) etc. may be inserted to increase transcriptional efficiency. Position of the enhancer sequence has not been found to be critical. Accordingly, the enhancer sequence may be inserted upstream, downstream or within the gene of interest.

Initiation signals are required for gene transcription and translation in procaryotic cells. For example, translation in *E. Coli* requires a Shine-Dalgarno (SD) sequence about 7–9 bases from the initiation codon (ATG) to provide a ribosomal binding site.

The gene of interest, and the elements described above, may be ligated, in appropriate orientation with the vector promoter and control elements, into the vector by methods known to those skilled in the art. For example, DNA can be ligated into a cloning vector which has complementary cohesive termini. If however, the complementary restriction sites are not present, the ends of the DNA molecule may be modified. Such modification includes producing blunt ends by digesting back single-stranded DNA termini or by filling the single stranded termini so that the ends can be blunt end ligated. Alternatively, any site desired may be produced by ligating nucleotide sequences onto the DNA termini. These ligated linkers may comprise specific chemically synthesized oligonucleotides encoding restriction sites. The DNA is then treated with restriction enzymes to cleave the terminal linker (but not the modified internal restriction sites) and ligated to the appropriate vector arms. In an alternative methods, the cleaved vector and DNA fragment may be modified by homopolymer tailing.

The vector is then introduced into the host cells. Depending upon the host cell used, transformation, transduction or transfection, is done using standard techniques appropriate to such cells. The calcium treatment employing calcium chloride, as described by Cohen, S. N., *Proc Natl Acad Sci (USA)* (1972) 69:2110, or methods described in *Molecular Cloning: A Laboratory Manual* (1988) Cold Spring Harbor Press, can be used for procaryotes or other cells which contain substantial cell wall barriers. Infection with *Agrobacterium tumefaciens* (Shaw, C. H., et al., *Gene* (1983) 23:315) is believed useful for certain plant cells. For mammalian cells without such cell walls, the calcium phosphate precipitation method of Graham and van der Eb, *Virology* (1978) 52:546 can be used. Transformations into yeast can be carried out according to the method of Van Solingen, P., et al., *J Bact* (1977) 130:946 and Hsiao, C. L., et al., *Broc Natl Acad Sci (USA)* (1979) 76:3829.

Transformants can be selected based upon the expression of one or more appropriate gene markers normally present in the vector, such as ampicillin or tetracycline resistance in pBR322 or thymidine kinase activity in eucaryotic host systems. Expression vectors may be derived from cloning vectors, which usually contain a marker function. Such cloning vectors may include, but are not limited to the following: SV40 and adenovirus, vaccinia virus vectors, insect viruses such as baculoviruses, yeast vectors, bacteriophage vectors such as lambda gt-WES-lambda B, Charon 28, Charon 4A, lambda gt-1-lambda BC, lambda gt-1-lambda B, M13mp7, M13mp8, M13mp9, or plasmid DNA vectors such as pBR322, pAC105, pVA51, pACYC177, pKH47, pACYC184, pUB110, pMB9, pBR325, Col E1, pSC101, pBR313, pML21, RSF2124, pCR1, RP4, pBR328 and the like.

The protein can be isolated using standard methods known to those skilled in the art. Such methods include, but are not limited to chromatography, centrifugation and differential solubilization.

Opacity associated proteins such as Oap A and Oap B, whether prepared synthetically or by recombinant methods, are encompassed by the present invention. Oap A includes, but is not limited to the amino acid sequence substantially as set forth in SEQ ID NO: 2. Oap B includes, but is not limited to the amino acid sequence substantially as set forth in SEQ ID NO: 3. Both amino acid sequences may include altered sequences in which functionally equivalent amino acid residues are substituted for residues within the sequence which do not affect the activity of the protein. For example, one or more amino acid residues may be substituted by another of similar polarity. At least 85% homology to the sequences set forth in SEQ ID NO: 2 and 3 are encompassed by the present invention.

The ability of opacity associated proteins to elicit a protective immune response may be tested using in vitro assays and animal model systems, such as those used to test antibodies to the capsular polysaccharide of type b *H. influenzae*. These systems have been found to closely correlated with the ability to elicit a protective immune response in human infants.

An in vitro complement mediated bactericidal assay system, Musher et al., 1983, *Infect. Immun.* 39:297–304; Anderson et al., 1972, *J. Clin. Invest.* 51:31–38; which has been used previously for measuring bactericidal activity of antibodies for PRP and lipopolysaccharide (LPS) against *H. influenzae* could be used to determine whether or not antibody directed against an opacity associated protein or fragment thereof has bactericidal activity against type b *H. influenzae* and non-typable *H. influenzae*. These assays can be performed against a relatively large number of clinical isolates of both typable and non-typable bacteria to determine whether a broad range of strains are killed.

Further data on the ability of opacity associated proteins, or fragments thereof, to elicit a protective antibody response may be generated by use of the infant rat meningitis model system. Smith et al., 1973, *Infect. Immun.* 8:278–290. Infant rats challenged before the sixth day of life, with a suitable dose of *H. influenzae* type b develop bacteremia and a fatal meningitis similar to that seen in human infants. If antibody which is bactericidal against a challenge strain is used to passively immunize infant rats prior to challenge, then they are protected from meningitis and death. Antibodies directed against the current vaccine for type b Haemophilus, PRP, are protective in the infant rat model system. Passive protection against type b Haemophilus meningitis could be demonstrated by immunizing infant rats with rabbit polyclonal anti-Oap A and/or Oap B antibody and subsequently challenging the rats with a lethal dose of *H. influenzae* type b.

Data on the ability of antibody for opacity associated proteins to protect against non-typable *H. influenzae* could be obtained using the chinchilla otitis media animal model system, Barenkamp et al., 1986, *Infect. Immun.* 52:572–78. In this animal model, chinchillas are challenged by inoculation of the inner ear canal with non-typable *H. influenzae*. An otitis media much like that seen in humans develops. Chinchillas, which have been immunized, either actively with non-typable *H. influenzae* outermembrane proteins, or passively with antibody directed against non-typable *H. influenzae* outermembrane proteins are protected against aural challenge with the bacteria, Barenkamp et al., supra. Specifically, immunization should inhibit colonization by *H. influenzae*. This animal model system could be used to demonstrate the ability of antibody to one or both opacity associated proteins to protect against non-typable *H. influenzae* and specifically to inhibit colonization of *H. influenzae*.

Passive immunization during fetal development may also be studies using this model. For example, a female chinchilla may be immunized against *H. influenzae* prior to or during gestation. Thereafter, the response of her offspring to challenge by *H. influenzae* is observed. Specifically inhibition of colonization by *H. influenzae* can be analyzed.

Vaccine formulations of the present invention are comprised of an opacity associated protein, such as Oap A and Oap B, whether recombinantly prepared, synthetically prepared, or isolated in substantially purified form in combination with any suitable vaccine adjuvant. Suitable adjuvants include, but are not limited to, surface active substances, e.g., hexadecylamine, octadecylamine, octadecyl amino acid esters, lysolecithin, dimethyldioctadecylammonium bromide, N, N-dicoctadecyl-N'-N-bis (2-hydroxyethyl-propane diamine), methoxyhexadecylglycerol, and pluronic polyols; plyamines, e.g., pyran, dextransulfate, poly IC, polyacrylic acid, carbopol; peptides, e.g., muramyl dipeptide, dimethylglycine, tuftsin; oil emulsions; and mineral gels, e.g., aluminum hydroxide and aluminum phosphate. The immunogen may also be incorporated into liposomes, or conjugated to polysaccharides and/or other polymers for use in a vaccine formulation.

In yet another embodiment of the invention, an opacity associated protein or fragments thereof, is a hapten, i.e., a molecule that is antigenic in that it reacts specifically or selectively with cognate antibodies, but is not immunogenic in that it cannot elicit an immune response. In such case, the hapten may be covalently bound to a carrier or immunogenic molecule; for example, a large protein such as protein serum albumin will confer immunogenicity to the hapten coupled to it. The hapten-carrier may be formulated for use as a subunit vaccine.

Vaccine formulations of the present invention may also be prepared as combination vaccines which include additional vaccine formulations to achieve an additive immunogenic response thereby augmenting present immunization regimes. For example, vaccine formulations of the present invention may be prepared in combination with other vaccine formulations which protect against *H. influenzae* type b such as commercially available vaccines prepared from the purified capsule of *H. influenzae* type b polyribosylribitol phosphate (PRP). In addition, the vaccine formulation may include formulation for targeting additional diseases such as diphtheria, *Neisseria meningitidis* and tetanus toxoid.

In accordance with some embodiments of the present invention are provided viral vaccines. Live recombinant viral vaccine or an inactivated recombinant viral vaccine are encompassed in aspects of the present invention. Recombinant viruses may be prepared as described above. Where the recombinant virus is infectious to the host to be immunized but does not cause disease, a live vaccine is preferred. The infectious recombinant virus when introduced into a host can express the opacity associated protein or proteins or polypeptide fragment thereof from its chimeric gene and thereby elicit an immune response against *H. influenzae* antigens. In cases where such an immune response is protective against subsequent *H. influenzae* infection, the live recombinant virus itself may be used in a preventative vaccine against *H. influenzae* infection. Production of such recombinant virus may involve both in vitro (e.g., tissue culture cells) and in vivo (e.g., natural host animal) systems. For instance, conventional methods for preparation and formulation of smallpox vaccine may be adapted for the formulation of live recombinant virus vaccine expressing one or both opacity associated proteins or polypeptides.

Multivalent live virus vaccines can be prepared from a single or a few infectious recombinant viruses that express epitopes of organisms that cause disease in addition to the epitopes of *H. influenzae* opacity associated proteins. For example, a vaccinia virus can be engineered to contain coding sequences for other epitopes in addition to those of *H. influenzae* opacity associated proteins. Such a recombinant virus itself can be used as the immunogen in a multivalent vaccine. Alternatively, a mixture of vaccinia or other viruses, each expressing a different gene encoding for different epitopes of opacity associated proteins and/or other epitopes of other disease causing organisms can be formulated in a multivalent vaccine.

Inactivated virus vaccine formulations may also be prepared. Inactivated vaccines are "dead" in the sense that their infectivity has been destroyed, usually by chemical treatment (e.g., formaldehyde). Ideally, the infectivity of the virus is destroyed without affecting the proteins which carry the immunogenicity of the virus. In order to prepare inactivated vaccines, large quantities of the recombinant virus expressing Oap proteins or polypeptides must be grown in culture to provide the necessary quantity of relevant antigens. A mixture of inactivated viruses which express different epitopes may be used for the formulation of "multivalent" vaccines. In certain instances, these "multivalent" inactivated vaccines may be preferable to live vaccine formulation because of potential difficulties with mutual interference of live viruses administered together. In either case, the inactivated recombinant virus or mixture of viruses should be formulated in a suitable adjuvant in order to enhance the immunological response to the antigens.

In still other embodiments of the present invention it is possible to confer short-term protection to a host by the administration of pre-formed antibody against an epitope of *H. influenzae*. Thus, the vaccine formulations can be used to produce antibodies for use in passive immunotherapy. Human immunoglobulin is preferred in human medicine because a heterologous immunoglobulin may provoke an immune response to its foreign immunogenic components. Such passive immunization could be used on an emergency basis for immediate protection of unimmunized individuals exposed to special risks, e.g., young children exposed to contact with bacterial meningitis patients. Alternatively, these antibodies can be used in the production of anti-idiotypic antibody, which in turn can be used as an antigen to stimulate an immune response against *H. influenzae* Oap epitopes.

Treatment regimes will vary with a patient's age, weight and condition. Immunization schedules are well known to those skilled in the art and will be easily modified for purposes of the present invention. For example a standard protocol for children provides for the admininstration of 2 primary doses of the vaccine followed by a booster at a later date.

Diagnostic assays are also encompassed by the present invention. For example, the opacity associated proteins and peptides of the present invention may be used as antigens in immunoassays for the detection of *H. influenzae* in various patient tissues and body fluids including, but not limited to: blood, spinal fluid, urine and sputum, etc. The antigens of the present invention may be used in any immunoassay system known in the art including, but not limited to, radioimmunoassays, ELISA assays, "sandwich" assays, precipitation reactions, gel diffusion precipitation reactions, immunodiffusion assays, agglutination assays, fluorescent immunoassays, protein A immunoassays and immunoelectrophoresis assays.

Furthermore, novel nucleotide sequence of the gene encoding opacity associated proteins and peptides of the present invention may be used to prepare probes for use in nucleic acid hybridization assays for the detection of *H. influenzae* in various patient body fluids, including but not limited to: blood, spinal fluid, urine and sputum. The nucleotide sequences of the present invention may be used to prepare probes useful in any nucleic acid hybridization assay system known in the art including, but not limited to Southern blots (Southern, 1975, *J. Mol. Biol.* 98:508); Northern blots (Thomas et al., 1980, *Proc. Nat'l Acad. Sci. USA* 77:5201–05); colony blots (Grunstein et al., 1975, *Proc. Nat'l Acad. Sci. USA* 72:3961–65) and capture plate assays. Probes of the present invention may range in length from about 10 to about 200 nucleotides. In preferred embodiments of the present invention, probes are from about 15 to about 100 nucleotides in length. In still other embodiments of the present invention probes are from about 15 to about 25 nucleotides in length.

Kits may be supplied comprising one or more probes which specifically hybridize to a gene coding for an opacity associated protein. Such probes may be appropriately labeled with detectable label or reagents for labeling purposes may be included. Kits comprising one or more peptides suitable for immunoassay systems described above are also encompassed in some aspects of the present invention.

The following examples are illustrative but are not meant to be limiting of the present invention.

EXAMPLES

Example 1

Bacterial Strains, Media, and Chemicals

*H. influenzae* strains used for the study are shown in Table 1. The strains were grown in brain-heart infusion (BHI) broth supplemented with 1.5% Files enrichment (Difco, Detroit). BHI plates were solidified with 1% agar. Colony morphology was determined using a stereo zoom dissecting microscope with a substage mirror and 100-W halogen illuminator. Colony morphology was assessed after incubation of agar plates for 14–16 h at 37° C. Chemicals were purchased from Sigma (St. Louis) unless otherwise specified.

TABLE 1

Genotype or characteristics of *H. influenzae* strains used in this study.

| Strain | Genotype or characteristics | Source or reference |
|---|---|---|
| Eagan | Serotype b clinical isolate | A. Smith (University of Washington, Seattle, WA) |
| Eagan-T | Transparent variant of Eagan | This study |
| Eagan-I | Intermediate opacity variant of Eagan | This study |
| Eagan-O | Opaque variant of Eagan | This study |
| Eagan-I-R | Intermediate opacity revertant of Eagan O | This study |
| Eagan-T-R | Transparent revertant of Eagan I-R | This study |
| Eagan 16K | Pilin⁻, Kan | Fuju 16K x Eagan |
| Eagan 16K-T | Transparent variant of Eagan 16K | This study |
| Eagan 16K-I | Intermediate opacity variant of Eagan 16K | This study |
| Eagan 16K-O | Opaque variant of Eagan 16K | This study |
| Eagan galE | galE, Kan | D. Maskell (Imperial College, Lon- don) |
| Fuju | Serotype b clinical isolate | Gilsdorf, and Ferrieri, *J. Infect. Disease*, 153:223–31 (1986) |
| Rat3Fuju | Opaque variant of Fuju | Gilsdorf, and Ferrieri, *J. Infect. Disease*, 153:223–31 (1986) |
| Fuju 16K | pilin⁻, Kan | J. Gilsdorf (University of Michigan, Ann Arbor) |
| Fuju 16K-T | Transparent variant of Fuju 16K | This study |
| Fnju-16K-I | Intermediate opacity variant of Fuju 16K | This study |
| Fuju 16K-O | Opaque variant of Fuju 16K | This study |
| Rd⁻T | Capsule-, type d isolate, Tn916ΔΣ(Erm') | Unpublished data |
| Rd⁻I | Intermediate opacity variant of Rd⁻T | Unpublished data |
| Rd⁻O | Opaque variant of Rd⁻1 | Unpublished data |
| Rd⁻/b+O1 | Type b capsule, O1 LPS pattern | Zwahlen, et al., *Microb. Pathog.*, 1:465–73 (1986) |
| Rd⁻/b+O2 | Type b capsule, O2 LPS pattern | Zwahlen, et al., *Microb. Pathog.*, 1:465–73 (1986) |
| Rd⁻/b+/I69 | Type b capsule, deep rough LPS | Zwahlen, et al., *J. Infect. Dis.*, 152:485–92 (1985) |
| RM7004 | Serotype b clinical isolate | Weiser, et al., *Infect. Immun.*, 57:3045–52 (1989) |
| RM7004-AH1-2 | lic 1⁻, Tet | Weiser, et al., *Infect. Immun.*, 58:3455–7 (1990) |
| RM7004-EX1 | lic 2⁻, Tet | Weiser, et al., *Infect. Immun.*, 58:3455–7 (1990) |
| RM7004-RVdel8 | lic 3⁻, Tet | Maskell, et al., *Mol. Microbiol.*, 5:1013–22 (1990) |

NOTE: Kan, kanamycin; Tet, tetracycline; LPS, lipopolysaccharide.

Strain Fuju 16K has a kanamycin resistance marker from Tn903 cloned into the Bg/II site in the major pilin gene. Gilsdorf, J. R., et al., *Infect Immunol.*, 1990, 58, 1063–72. Chromosomal DNA from Fuju 16K was used to transform strain Eagan by the method of Herriot et al. Herriot et al., *J Bacteriol* 101: 517–524 (1970) to obtain kanamycin-resistant strain Eagan 16K. When appropriate *H. influenzae* strains were maintained on kanamycin (20 µg/mL) or erythromycin (10 µg/mL).

On gross examination with oblique illumination on translucent, solid media without magnification, colonies of *H. influenzae* Eagan of a clonal origin varied in appearance. Observation with transmitted light and magnification revealed three distinct colony morphologies that differed in color and opacity. The most transparent (T) colonies had a bluish hue, the intermediate (I) colonies appeared whitish, and the most opaque (O) forms had an orange tint.

Example 2

Relationship between Opacity and *H. influenzae* Pathogenesis

Figure 2B:
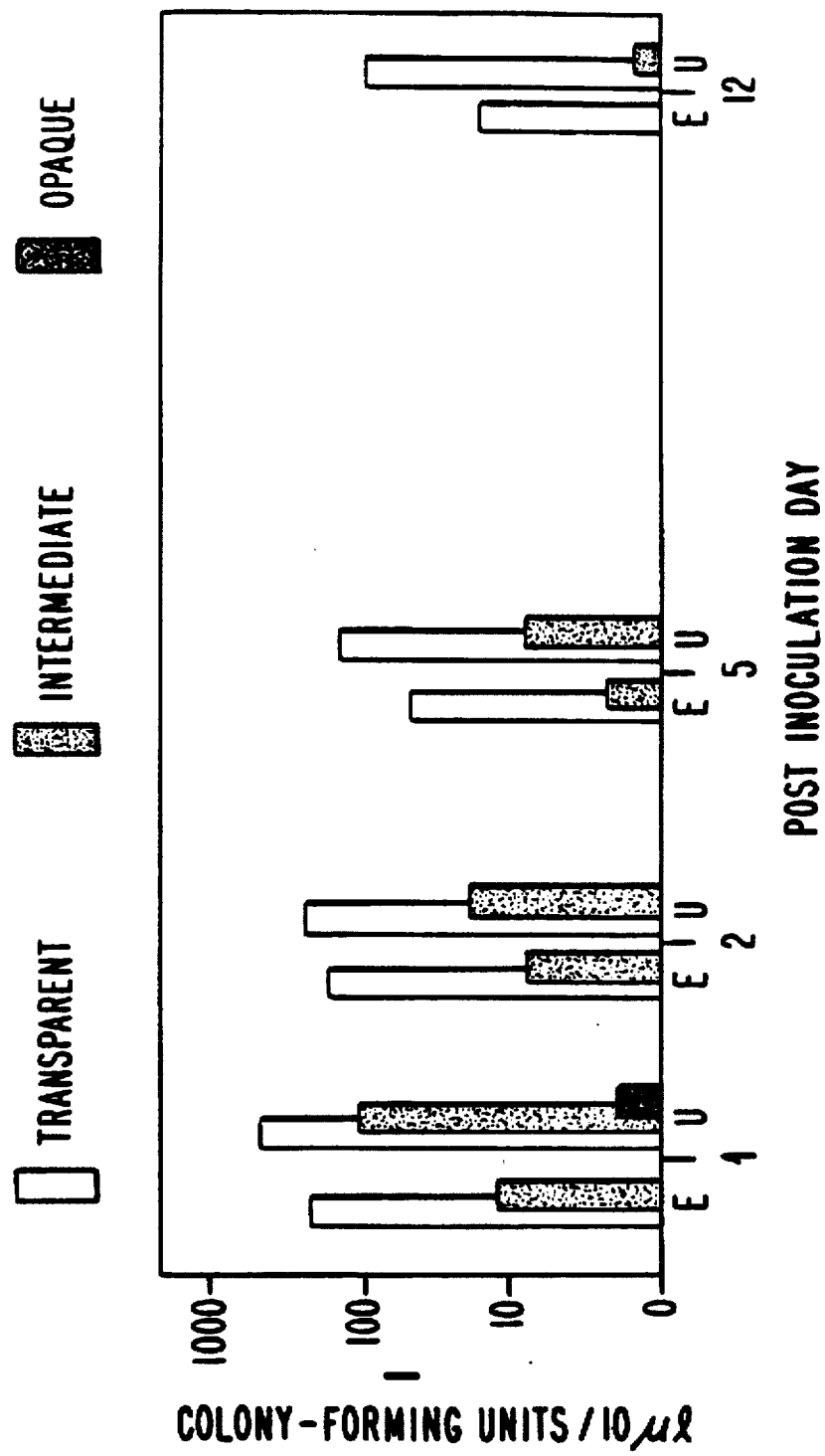
Figure 2C:
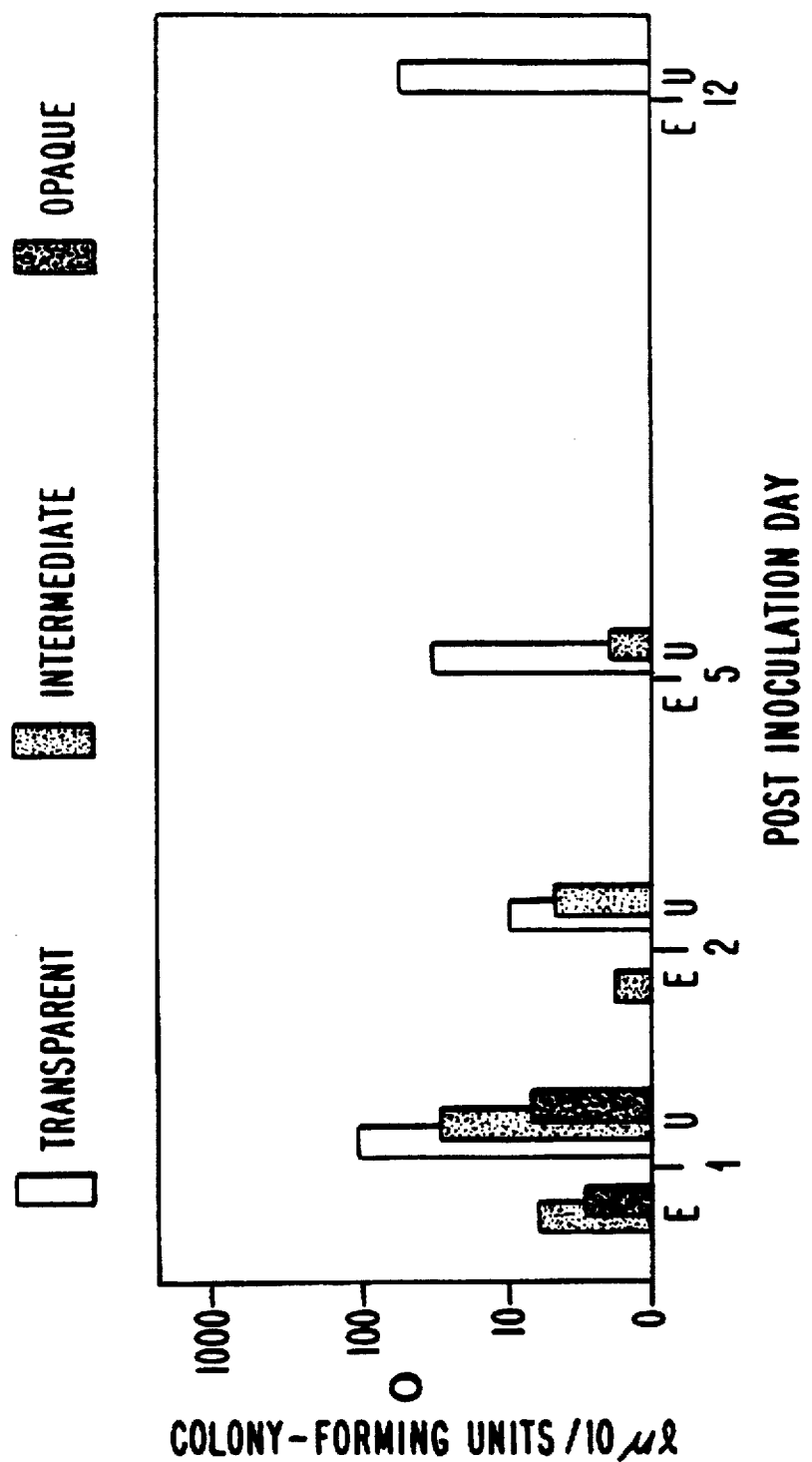

The infant rat model of *H. influenzae* colonization and bacteremia, which mimics natural infection during childhood, was used to investigate the relationship between opacity phase variation and colonization. Five day old infant rats received intranasal inoculum of $10^5$ colony-forming units (cfu) of *H. influenzae*. Serial washes of nasopharynx were cultured to determined quantity and phenotype of organisms colonizing nasal mucosa 1, 2, 5, and 12 days after inoculation. Animals received mutant strains Eagan 16K (E) or Fuju 16K (U) in which the major pilin gene had been inactivated by insertion of a kanamycin resistance marker. This was done to eliminate any unrecognized contribution of fimbriae which has been implicated as a factor in colonization; Weber et al, *Infect Immun* 59: 4724–4728 (1991); and to provide a means of selecting against contaminants in nasal washes. For each strain, 20 pups received inoculum of >95% of single opacity phenotype (transparent [T], intermediate [I] and opaque [O] as indicated). Results are shown in FIG. 2.

The O phenotype was impaired in its ability to colonize the nasopharynx in contrast to the T and I variants. Of the few isolates obtained from nasal washes of pups receiving the O inoculum, all had either the T or I phenotype by 48 h after challenge (FIG. 2(O)). The T variant colonized the nasopharynx most efficiently, as assessed by the number of culture-positive pups and density of colonization (FIG. 2(T)). By 24 h after administration, most of the I inoculum had shifted in phenotype to the T form (FIG. 2(I)). At 12 days after inoculation, at the time of weaning >98% of isolates were of the T phenotype regardless of the original phenotype of the inoculum. Results for both strains were similar. Further evidence that the T variant is best suited to survival in the nasopharynx comes from experiments in which a mixed inoculum consisting of equal numbers of Eagan 16K-T, -I, and -O organisms were administered. Again, most colonies from nasopharyngeal washes were of the T phenotype by 24 h after inoculation, and no O variants were identified (data not shown). Values are arithmetic mean number of cfu in 10 µl of nasal wash of 20 pups. These results suggest that *H. influenzae* type b can vary between two phenotypes, one adapted for nasopharyngeal colonization (transparent) and the other for systemic infection (opaque).

Example 3

Identification of Opaque Transformant H175

A spontaneous variant of *H. influenzae* strain Rd with an opaque phenotype, denoted H175, was obtained by screening a large number of colonies for altered morphology. It was found that chromosomal DNA from H175 was able to transform Rd to the opaque phenotype by the method of Herriot et al., *J. Bacteriol.*, 101:517–524 (1970).

Example 4

Construction of a Genomic Library of H175 in λEMBL3

The genetic locus determining the expression of colony opacity was isolated as follows. Genomic DNA was prepared substantially as described by Hoiseth, et al., *Infect. Immun.*, 49:389–395 (1985). Chromosomal DNA from H175 (50 µg) was partially digested with Sau3A1 and size fractionated on a sucrose gradient. Sambrook, et al., *Molecular cloning: A laboratory manual.* Cold Spring Harbor Press, Cold Spring Harbor, N.Y. Samples which contained fragments ranging in size from 9 kB to 15 kB were pooled, ethanol precipitated, and used for ligation into λEMBL3 arms cut with BamH1 (Stratagene, La Jolla, Calif.). The ligation mixture was then packaged and used to infect *E. Coli* strain XL-Blue MRA (P2) (Stratagene, La Jolla, Calif.). DNA was prepared by the plate lysate method obtained from pools of λEMBL3 plaques. Sambrook, et al., *Molecular cloning: A laboratory manual.* Cold Spring Harbor Press, Cold Spring Harbor, N.Y. When DNA from a pooled group of plaques was shown to possess tranforming activity to the opaque phenotype, it was further subdivided until a single clone was identified.

Example 5

Cloning and Sequencing of the *H. influenzae* Opacity Locus

A single λEMBL3 clone with tranforming activity was mapped using various restriction endonucleases (New England Biolabs, Beverly, Mass.). Fragments were subcloned into vector pACYC184 and transformed into frozen competent DH5α (supE44ΔlacU169(ø80lacZM15) hsdR17recA1endA1gyrA96thi-1relA1) and screened for tranforming activity. Plasmid DNA was isolated by the alkaline lysis method. Birnboim and Doly, *Nucleic Acid Res.*, 7:1513–1518 (1979). These constructs were transformed into Rd and the kanamycin resistant transformants screened for opacity. Insertion of the marker into a EcoRi site resulted in a loss of the transparent phenotype. The region flanking the EcoRI site in PE195 was sequenced using M13 bacteriophage. Sanger, et al., *Proc. Natl. Acad. Sci. USA*, 74: 5463–5467 (1977). The sequences were analyzed using the software package of the Genetics Computer Group. Databases were searched using National Center for Biotechnology blast program. The DNA sequence of oapA and oapB, with the putative amino acid sequences, are set forth in FIG. 1.

Example 6

The oapA Gene is Essential to Colonization

Figure 3A:
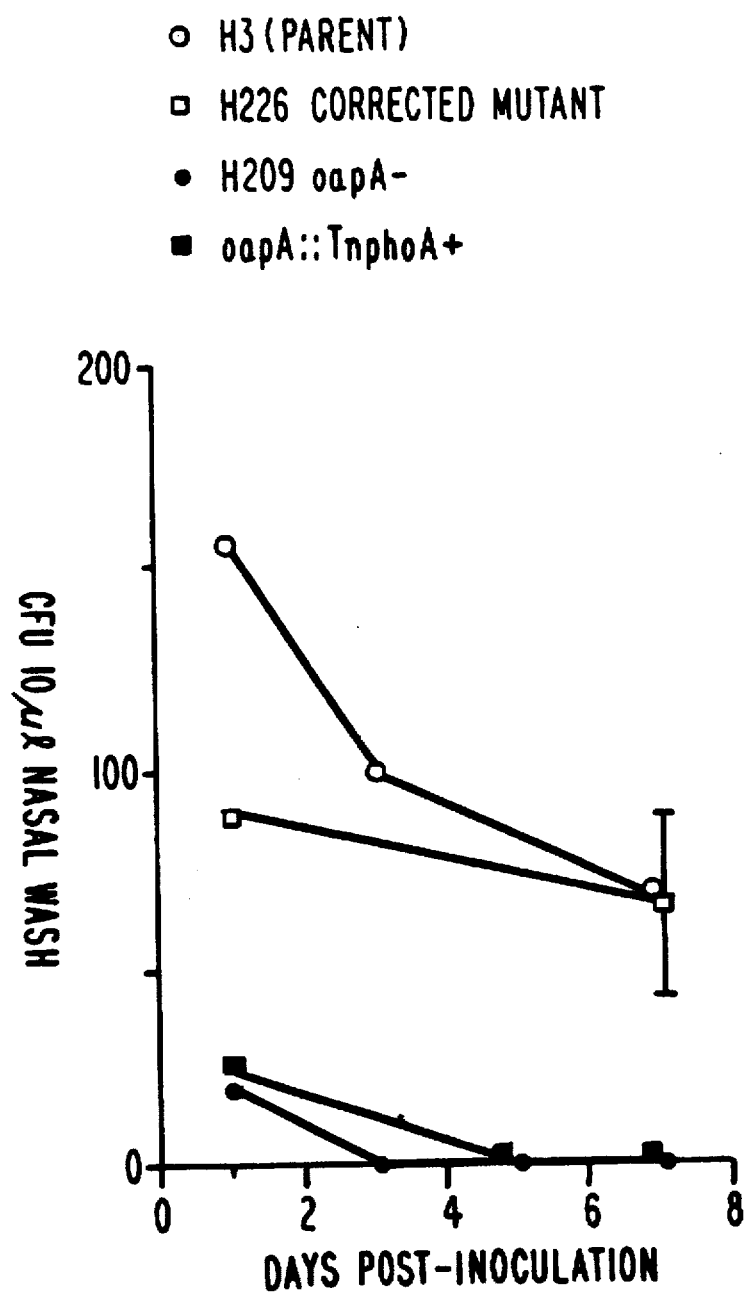
FIG. 3A is a graph showing nasopharyngeal colonization of the uncapsulated strain of *H. influenzae*, H3 (○), strain H209 (oapA⁻) (●), strain H226 (corrected mutant) (□) and oapA::TnphoA⁺ (■).
Figure 3B:
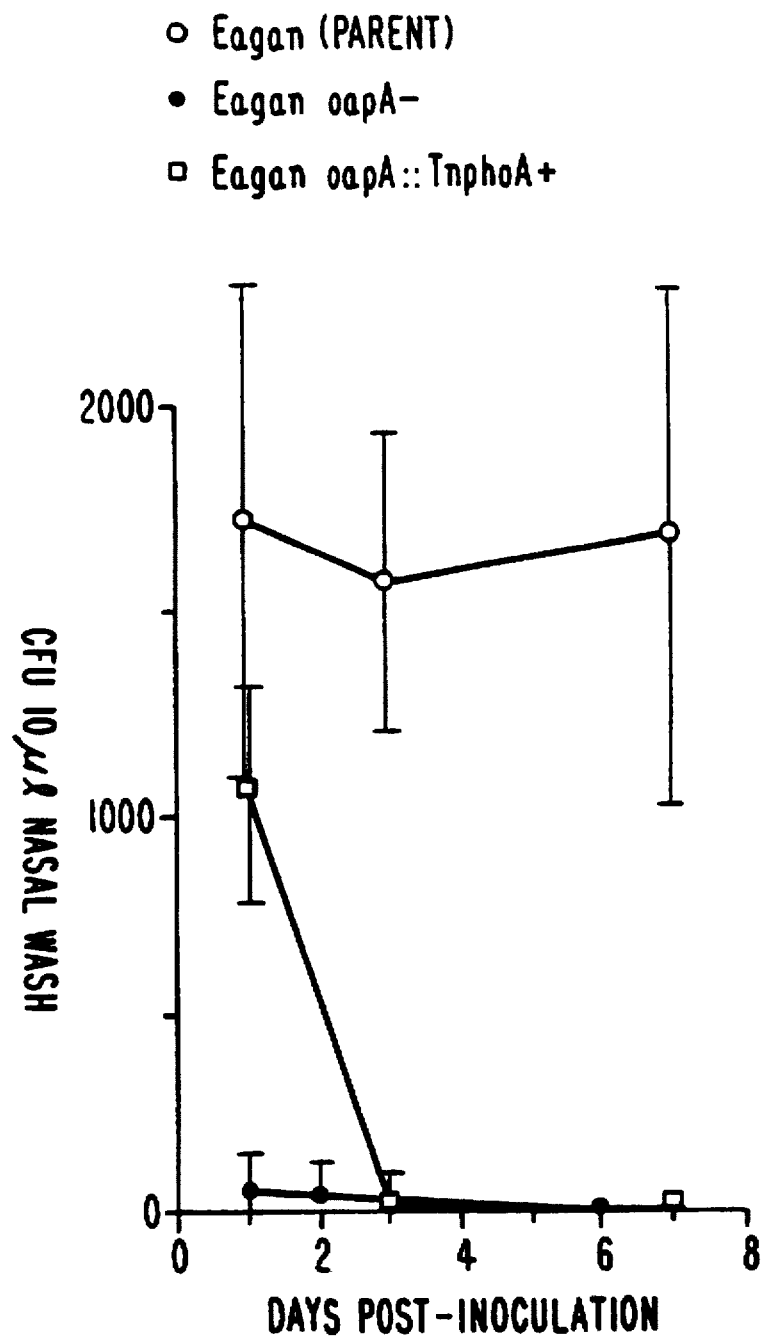
FIG. 3B is a graph showing nasopharyngeal colonization of the capsulated strain of *H. influenzae*, Eagan (○), Eagan oapA⁻ mutant (●) and Eagan oapA::TnphoA⁺ (□).

Using the infant rat model as described in Example 2, rats were inoculated with strains of mutant and wild type capsular (Eagan) and uncapsulated (H3) *H. influenzae*. Mutant strains were prepared substantially as described in Example 5 by transforming bacteria strains with a plasmid construct carrying the oapA mutation. As shown in FIG. 3, capsular (FIG. 3B) and uncapsulated (FIG. 3A) wild type strains colonized the nasopharynyx while mutant strains lacking the oapA gene did not. The colonization ability of mutant strains was restored by addition of the oapA gene.

Example 7

Colorimetric Assays Show that the OapA Protein is a Surface Protein

*E.Coli* hosts (kan$^r$) were transformed with a plasmid carrying the oapA gene. For detection purposes, a gene fusion was prepared by introducing a transposon carrying a gene for alkaline phosphatase (PhoA$^+$Kan$^r$) and selecting for plasmids in which the PhoA gene was inserted in frame with the oapA gene. It was expected that for transformants in which the PhoA gene was in frame with the oapA gene, if oapA was expressed on the surface of the cell, then OapA$^+$PhoA$^+$ transformants would be kanamycin resistant and would be blue in colorimetric assays. Blue colonies were observed, thereby establishing that opaA is expressed on the cell surface.

Example 8

Colorimetric Assay shows that the OapA Protein is Expressed on the Surface of *H. influenzae* Cells The construct from positive transformants from Example 7 were used to transform *H. influenzae*. *H. influenzae* transformants were positive for PhoA and kan$^r$ (as evidenced by blue colony formation).

Example 9

Western Blot Analysis Shows OapA Protein Expression in Both *E. Coli* and *H. influenzae*

Membrane proteins were divided into sarcosyl soluble and insoluble fractions by centrifugation and run on 10% separating SDS-PAGE 5 stacking gene with 1× SDS-PAGE buffer at 152V. The proteins were transferred to nitrocellulose at 1 Amp for 1 hour. Western blots were also performed in accordance with standard protocols. The filter was incubated for 2 hours at 25° C. with a 1:500 dilution of antibody recognizing PhoA (rabbit anti-BAP) in tris saline blotting buffer (TSBB). Thereafter the filter was washed 5× in TSBB. The filter was incubated for 1 hour at 25° C. with a secondary antibody (anti-rabbit antibody conjugate) at 1:3000 dilution in TSBB, washed 4 times in TSBB and dried. The western blot showed that oapA was expressed in the outermembrane (sarcosyl insoluble fraction) by both *E. Coli* and *H. influenzae*.

Example 10

Immunoblotting shows that OapA is Expressed in the Outermembrane of *H. influenzae*

Bacterial cell membranes are comprised of an inner layer and an outer layer. For purposes of eliciting a immunogenic response, it is generally accepted that proteins which are expressed on the outer membrane should be used as antigens since it has not yet been shown that antibodies can recognize proteins of the cell interior. To test whether oapA was expressed on the outermembrane, nitrocellulose membrane was applied to SBHI$_{kan20}$+40 mL xP/40mL BHI plates streaked with two strains of *H. influenzae*, strain H238 (oapA$^+$PhoA$^+$) and strain H228 (oapA$^-$PhoA$^+$). The membrane was washed 3× in TSBB. The filter was incubated for 2 hours at 25° C. with a 1:1000 dilution of antibody recognizing PhoA (rabbit anti-BAP) in TSBB. Thereafter the filter was washed 5× in TSBB. The filter was incubated for 1 hour at 25° C. with a secondary antibody (anti-rabbit antibody conjugate) at 1:300 dilution in TSBB, washed 4 times in TSBB and once in alkaline phosphate buffer. Color was developed by adding 66 μl nitroblue tetrazolium (NBT) X 33 μl 5-bromo-4-chloro-3-indoly-phosphate toluidine salt (Sigma, St. Louis, Mo.) to 10 ml alkaline phosphate buffer at room temperature. Strain H238 exhibited blue color while Strain H228 did not. Therefore, the oapA protein is expressed on the outermembrane and is available to recognition by antibody.

---

What is claimed is:

1. A substantially pure opacity associated protein of *H. influenzae* having the sequence of SEQ ID NO:2 or SEQ ID NO:3.

2. A protein produced from an isolated DNA sequence having the sequence of SEQ ID NO:1.

3. An opacity associated protein produced by recombinant host cells transformed with the DNA having the sequence of SEQ ID NO:1 operably linked to regulatory control sequences, which cells express at least one opacity associated protein.

4. A vaccine composition for the prevention of *Haemophilus influenzae* infection in a mammal comprising an immunogenically effective amount of at least one substantially pure opacity associated protein from *Haemophilus influenzae* having the sequence of SEQ ID NO:2 or SEQ ID NO:3 and a physiologically acceptable carrier.

* * * * *

SEQUENCE LISTING ( 1 ) GENERAL INFORMATION:

( i i i ) NUMBER OF SEQUENCES: 3

( 2 ) INFORMATION FOR SEQ ID NO:1:

( i ) SEQUENCE CHARACTERISTICS:
        ( A ) LENGTH: 2100 base pairs
        ( B ) TYPE: nucleic acid
        ( C ) STRANDEDNESS: double
        ( D ) TOPOLOGY: unknown ( i i ) MOLECULE TYPE: DNA (genomic)

( i x ) FEATURE:
        ( A ) NAME/KEY: CDS
        ( B ) LOCATION: 1553..2005

( i x ) FEATURE:
        ( A ) NAME/KEY: CDS
        ( B ) LOCATION: 209..1492

( x i ) SEQUENCE DESCRIPTION: SEQ ID NO:1:

```
AAATCTATAA  AACCTTGCAA  TCTCTGACTT  CTGGCTATCT  TGTTCCTAAA  CTTGCACGAG         60
```

-continued

```
AAATTGCGGG CGAGCCAAAT AAGACTTTAT ACGCAGAATA AGATCCGATA AAATACACAT        120

AATTTTTTCG CCGCACTTTT GAGCTTCTCA ATTTTGTGGC TAATTAATAT AAATAAGAAC        180

AAGCATCAGA GGCAATCCAG TGAATTCT ATG GAT AAA AAT CAA CAA TCA TCT           232
                               Met Asp Lys Asn Gln Gln Ser Ser
                                 1               5

CAA AAT GAA TTG GAT TTA GGG CTT AAT CAA GAG CCA ATT ACA CCA AAG          280
Gln Asn Glu Leu Asp Leu Gly Leu Asn Gln Glu Pro Ile Thr Pro Lys
        10              15                  20

AAA ACA ATT CAG CCA AGT TCG TCA ATT TTA GGT AAA GCA AAA GGG TTA          328
Lys Thr Ile Gln Pro Ser Ser Ser Ile Leu Gly Lys Ala Lys Gly Leu
 25              30                  35                      40

TTT GCC AAA AAA AAT CAC GTG CAA ACT AAC TTT CAG CAA CGT AAA GAA          376
Phe Ala Lys Lys Asn His Val Gln Thr Asn Phe Gln Gln Arg Lys Glu
                 45                  50                  55

CCT ACT TTT GGC GAT TCA TCA ACG CAA GAA AAT GAT CCT TTA ATT CCG          424
Pro Thr Phe Gly Asp Ser Ser Thr Gln Glu Asn Asp Pro Leu Ile Pro
             60                  65                  70

AGT GAA AAT TTG AAA AAA GTG CAA AAG CCT GTT CTT CAA ACT TCT TCC          472
Ser Glu Asn Leu Lys Lys Val Gln Lys Pro Val Leu Gln Thr Ser Ser
         75                  80                  85

ACA GAA GAA AAT ATT TCT GCG GTT GAT GAA GAA ATC AGT GCT GAA AAT          520
Thr Glu Glu Asn Ile Ser Ala Val Asp Glu Glu Ile Ser Ala Glu Asn
     90                  95                 100

AAC GCG GAT GAA CCC GTC GAA AAG GCT GAA AAA CCT ATT TTA GCT CAA          568
Asn Ala Asp Glu Pro Val Glu Lys Ala Glu Lys Pro Ile Leu Ala Gln
105                 110                 115                 120

CCA GAA AAA TGG AAA ATA TTA CAA GTA TTG CCA GCA AAA CAT CGC CGT          616
Pro Glu Lys Trp Lys Ile Leu Gln Val Leu Pro Ala Lys His Arg Arg
                125                 130                 135

TTA TTT ATG GCT ATT TTT GTG TTG GTT ATT TTA TTG ATT ATT TTC TTC          664
Leu Phe Met Ala Ile Phe Val Leu Val Ile Leu Leu Ile Ile Phe Phe
            140                 145                 150

GCA TTA AAA CCA AGT TCT GAC ACC GTT GAG TCT TTT ACT CAA TCT AAC          712
Ala Leu Lys Pro Ser Ser Asp Thr Val Glu Ser Phe Thr Gln Ser Asn
        155                 160                 165

AGC AAT GAA GTT CCT GTG CAG TTC CAA TCG TTA GAT CAA AGT CAG CCA          760
Ser Asn Glu Val Pro Val Gln Phe Gln Ser Leu Asp Gln Ser Gln Pro
    170                 175                 180

CTG GAA ACC ACG ATT TTA GAT AAT CCT CCT GCA CAA AAT CAA ATG GCT          808
Leu Glu Thr Thr Ile Leu Asp Asn Pro Pro Ala Gln Asn Gln Met Ala
185                 190                 195                 200

GTA GAA CAA GCT AAC CAA TCT GAA TTT GCA CCA AAA GCA GAG GAA GCG          856
Val Glu Gln Ala Asn Gln Ser Glu Phe Ala Pro Lys Ala Glu Glu Ala
                205                 210                 215

GCG AAT AAT ACG ACG GCT CAA AAC CCA TTA GTA GAA AAT GCG CCA ATG          904
Ala Asn Asn Thr Thr Ala Gln Asn Pro Leu Val Glu Asn Ala Pro Met
            220                 225                 230

CAA CAA AAT GTT GTT CAA TCT CCA AGT CAA ATG CCA AAT GAA ATG GCT          952
Gln Gln Asn Val Val Gln Ser Pro Ser Gln Met Pro Asn Glu Met Ala
        235                 240                 245

GCG GCA TCT GTT GCG CCT ATG CAA CCA GCT CAA GCG GAA CAG CCA AAA         1000
Ala Ala Ser Val Ala Pro Met Gln Pro Ala Gln Ala Glu Gln Pro Lys
    250                 255                 260

GCA ACT GTG CCA GTT CAG CCG ATG AAA AAA GCG GTA GAG CCA CAA CTT         1048
Ala Thr Val Pro Val Gln Pro Met Lys Lys Ala Val Glu Pro Gln Leu
265                 270                 275                 280

GCG CAT AAA GAT ACA GTG AAA AAA GAA GTG AAA GTG GCG GAG AAA GCA         1096
Ala His Lys Asp Thr Val Lys Lys Glu Val Lys Val Ala Glu Lys Ala
                285                 290                 295
```

```
CAG GCT CCA GCA AAA GCA ACG GAA CAA AAC GTC GCT AAA ACA GCA GGA        1144
Gln Ala Pro Ala Lys Ala Thr Glu Gln Asn Val Ala Lys Thr Ala Gly
            300                 305                 310

AAC GCA CCG ATT GTT GAA GCC AAA CCT GTT CAA GCT AAA AAA GAA AAG        1192
Asn Ala Pro Ile Val Glu Ala Lys Pro Val Gln Ala Lys Lys Glu Lys
            315                 320                 325

AAA GTT CAA ATC GTT GAT GCA AAA CCT GTG AGT AAA TCT ACA GCT TCT        1240
Lys Val Gln Ile Val Asp Ala Lys Pro Val Ser Lys Ser Thr Ala Ser
        330                 335                 340

CGC CTT TCA GCA AAA ACA TTA ACT GTG CCG AAA GGT GTT TCG CTG ATG        1288
Arg Leu Ser Ala Lys Thr Leu Thr Val Pro Lys Gly Val Ser Leu Met
345                 350                 355                 360

CAA CTC TTC CGT GAT AAT CAA CTT AAT ATT TCC GAT GTA AAC GCA ATG        1336
Gln Leu Phe Arg Asp Asn Gln Leu Asn Ile Ser Asp Val Asn Ala Met
                365                 370                 375

AGC AAA GCG ACA GGG GCG GGA AAT GTT TTA AGT AGC TTT AAA TCT GGC        1384
Ser Lys Ala Thr Gly Ala Gly Asn Val Leu Ser Ser Phe Lys Ser Gly
            380                 385                 390

GAT AAA GTA ACG GTA TCT GTG AAT AAT CAA GGG CGA GTA AAT GAA ATG        1432
Asp Lys Val Thr Val Ser Val Asn Asn Gln Gly Arg Val Asn Glu Met
        395                 400                 405

CGT TTA TCC AAT GGT GCG CGT TTT GTG CGT CAG TCT GAT GGT TCT TAT        1480
Arg Leu Ser Asn Gly Ala Arg Phe Val Arg Gln Ser Asp Gly Ser Tyr
410                 415                 420

CAA TAT AAA AAA TAATTTTTG GGCGAGTAAT CGCCTTTTTC TTTTTAAGTT             1532
Gln Tyr Lys Lys
425

CTTTTCTCAA GGTAGGATTT ATG TTG AAA AAA ACA TCT CTT ATT TTT ACC          1582
                     Met Leu Lys Lys Thr Ser Leu Ile Phe Thr
                      1               5                   10

GCA CTT TTA ATG ACT GGC TGT GTG CAA AAT GCG AAT GTA ACA ACA CCT        1630
Ala Leu Leu Met Thr Gly Cys Val Gln Asn Ala Asn Val Thr Thr Pro
            15                  20                  25

CAA GCG CAA AAA ATG CAA GTA GAA AAA GTG GAT AAA GCC TTA CAA AAA        1678
Gln Ala Gln Lys Met Gln Val Glu Lys Val Asp Lys Ala Leu Gln Lys
        30                  35                  40

GGC GAA GCT GAT CGA TAT TTA TGT CAA GAT GAT AGA GTT GTT CGT GTT        1726
Gly Glu Ala Asp Arg Tyr Leu Cys Gln Asp Asp Arg Val Val Arg Val
45                  50                  55

GTA CAC GCC ACG CAT AAA AAA TAC AAA AAA AAT TTG CAT TAT GTT ACT        1774
Val His Ala Thr His Lys Lys Tyr Lys Lys Asn Leu His Tyr Val Thr
            60                  65                  70

GTC ACT TTT CAA GGC GTA TCA GAA AAA CTA ACC TTA ATG ATT TCT GAA        1822
Val Thr Phe Gln Gly Val Ser Glu Lys Leu Thr Leu Met Ile Ser Glu
75                  80                  85                  90

CGT GGT AAA AAT TAC GCC AAT ATT CGT TGG ATG TGG CAA GAG CGT GAT        1870
Arg Gly Lys Asn Tyr Ala Asn Ile Arg Trp Met Trp Gln Glu Arg Asp
            95                  100                 105

GAT TTT AGT ACG CTA AAA ACG AAT CTC GGC GAA ATT TTA GCA ACG CAA        1918
Asp Phe Ser Thr Leu Lys Thr Asn Leu Gly Glu Ile Leu Ala Thr Gln
        110                 115                 120

TGT GTC TCA CAA ACA AGT GAA CGC TTA TCT GAC AAT AAT CGT GCA AAG        1966
Cys Val Ser Gln Thr Ser Glu Arg Leu Ser Asp Asn Asn Arg Ala Lys
125                 130                 135

CGA ACT TCA ACG TGG TTT TGT TTT GCA TCG TCG CCC TTA TAGTGAAACG         2015
Arg Thr Ser Thr Trp Phe Cys Phe Ala Ser Ser Pro Leu
140                 145                 150

AGCTTATTGG TAGATTTATT CACTGAAGAA AGTGGGCGTT TAACCGTGAT TGCAAAAGGG      2075

GCGCGGGCAA AGCGTTCATC TTGGA                                            2100
```

( 2 ) INFORMATION FOR SEQ ID NO:2:

( i ) SEQUENCE CHARACTERISTICS:
        ( A ) LENGTH: 428 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

```
Met Asp Lys Asn Gln Gln Ser Ser Gln Asn Glu Leu Asp Leu Gly Leu
 1               5                  10                  15
Asn Gln Glu Pro Ile Thr Pro Lys Lys Thr Ile Gln Pro Ser Ser Ser
             20                  25                  30
Ile Leu Gly Lys Ala Lys Gly Leu Phe Ala Lys Lys Asn His Val Gln
         35                  40                  45
Thr Asn Phe Gln Gln Arg Lys Glu Pro Thr Phe Gly Asp Ser Ser Thr
     50                  55                  60
Gln Glu Asn Asp Pro Leu Ile Pro Ser Glu Asn Leu Lys Lys Val Gln
 65                  70                  75                  80
Lys Pro Val Leu Gln Thr Ser Ser Thr Glu Glu Asn Ile Ser Ala Val
                 85                  90                  95
Asp Glu Glu Ile Ser Ala Glu Asn Asn Ala Asp Glu Pro Val Glu Lys
            100                 105                 110
Ala Glu Lys Pro Ile Leu Ala Gln Pro Glu Lys Trp Lys Ile Leu Gln
        115                 120                 125
Val Leu Pro Ala Lys His Arg Arg Leu Phe Met Ala Ile Phe Val Leu
    130                 135                 140
Val Ile Leu Leu Ile Ile Phe Phe Ala Leu Lys Pro Ser Ser Asp Thr
145                 150                 155                 160
Val Glu Ser Phe Thr Gln Ser Asn Ser Asn Glu Val Pro Val Gln Phe
                165                 170                 175
Gln Ser Leu Asp Gln Ser Gln Pro Leu Glu Thr Thr Ile Leu Asp Asn
            180                 185                 190
Pro Pro Ala Gln Asn Gln Met Ala Val Glu Gln Ala Asn Gln Ser Glu
        195                 200                 205
Phe Ala Pro Lys Ala Glu Glu Ala Ala Asn Asn Thr Thr Ala Gln Asn
    210                 215                 220
Pro Leu Val Glu Asn Ala Pro Met Gln Gln Asn Val Val Gln Ser Pro
225                 230                 235                 240
Ser Gln Met Pro Asn Glu Met Ala Ala Ser Val Ala Pro Met Gln
                245                 250                 255
Pro Ala Gln Ala Glu Gln Pro Lys Ala Thr Val Pro Val Gln Pro Met
            260                 265                 270
Lys Lys Ala Val Glu Pro Gln Leu Ala His Lys Asp Thr Val Lys Lys
        275                 280                 285
Glu Val Lys Val Ala Glu Lys Ala Gln Ala Pro Ala Lys Ala Thr Glu
    290                 295                 300
Gln Asn Val Ala Lys Thr Ala Gly Asn Ala Pro Ile Val Glu Ala Lys
305                 310                 315                 320
Pro Val Gln Ala Lys Lys Glu Lys Lys Val Gln Ile Val Asp Ala Lys
                325                 330                 335
Pro Val Ser Lys Ser Thr Ala Ser Arg Leu Ser Ala Lys Thr Leu Thr
            340                 345                 350
Val Pro Lys Gly Val Ser Leu Met Gln Leu Phe Arg Asp Asn Gln Leu
        355                 360                 365
```

```
Asn  Ile  Ser  Asp  Val  Asn  Ala  Met  Ser  Lys  Ala  Thr  Gly  Ala  Gly  Asn
     370                 375                      380

Val  Leu  Ser  Ser  Phe  Lys  Ser  Gly  Asp  Lys  Val  Thr  Val  Ser  Val  Asn
385                      390                 395                           400

Asn  Gln  Gly  Arg  Val  Asn  Glu  Met  Arg  Leu  Ser  Asn  Gly  Ala  Arg  Phe
               405                      410                      415

Val  Arg  Gln  Ser  Asp  Gly  Ser  Tyr  Gln  Tyr  Lys  Lys
               420                      425
```

(2) INFORMATION FOR SEQ ID NO:3:

(i) SEQUENCE CHARACTERISTICS:
        (A) LENGTH: 151 amino acids
        (B) TYPE: amino acid
        (D) TOPOLOGY: linear (ii) MOLECULE TYPE: protein (xi) SEQUENCE DESCRIPTION: SEQ ID NO:3:

```
Met  Leu  Lys  Lys  Thr  Ser  Leu  Ile  Phe  Thr  Ala  Leu  Leu  Met  Thr  Gly
1                   5                   10                       15

Cys  Val  Gln  Asn  Ala  Asn  Val  Thr  Thr  Pro  Gln  Ala  Gln  Lys  Met  Gln
               20                       25                       30

Val  Glu  Lys  Val  Asp  Lys  Ala  Leu  Gln  Lys  Gly  Glu  Ala  Asp  Arg  Tyr
          35                       40                  45

Leu  Cys  Gln  Asp  Asp  Arg  Val  Val  Arg  Val  Val  His  Ala  Thr  His  Lys
     50                  55                       60

Lys  Tyr  Lys  Lys  Asn  Leu  His  Tyr  Val  Thr  Val  Thr  Phe  Gln  Gly  Val
65                       70                  75                            80

Ser  Glu  Lys  Leu  Thr  Leu  Met  Ile  Ser  Glu  Arg  Gly  Lys  Asn  Tyr  Ala
                    85                  90                            95

Asn  Ile  Arg  Trp  Met  Trp  Gln  Glu  Arg  Asp  Asp  Phe  Ser  Thr  Leu  Lys
               100                      105                      110

Thr  Asn  Leu  Gly  Glu  Ile  Leu  Ala  Thr  Gln  Cys  Val  Ser  Gln  Thr  Ser
          115                 120                      125

Glu  Arg  Leu  Ser  Asp  Asn  Asn  Arg  Ala  Lys  Arg  Thr  Ser  Thr  Trp  Phe
     130                 135                      140

Cys  Phe  Ala  Ser  Ser  Pro  Leu
145                 150
```